US006804787B2

(12) United States Patent
Dick

(10) Patent No.: US 6,804,787 B2
(45) Date of Patent: Oct. 12, 2004

(54) MANAGING DATA IN COMPLIANCE WITH REGULATED PRIVACY, SECURITY, AND ELECTRONIC TRANSACTION STANDARDS

(75) Inventor: Richard S. Dick, Alpine, UT (US)

(73) Assignee: Verisma Systems, Inc., Pueblo, CO (US)

( * ) Notice: Subject to any disclaimer, the term of this patent is extended or adjusted under 35 U.S.C. 154(b) by 0 days.

(21) Appl. No.: 10/192,175

(22) Filed: Jul. 9, 2002

(65) Prior Publication Data

US 2003/0217290 A1 Nov. 20, 2003

Related U.S. Application Data

(60) Provisional application No. 60/380,679, filed on May 15, 2002.

(51) Int. Cl.[7] ............................. G06F 17/60; H04L 9/00
(52) U.S. Cl. ........................... 713/201; 705/3; 713/165; 707/9
(58) Field of Search ................................. 713/200, 201, 713/164, 165; 707/9, 200, 201, 204; 705/1–4, 50–52; 709/225, 226, 227, 229

(56) References Cited

U.S. PATENT DOCUMENTS

| | | | | |
|---|---|---|---|---|
| 6,289,460 | B1 * | 9/2001 | Hajmiragha | 713/200 |
| 2001/0041991 | A1 * | 11/2001 | Segal et al. | 705/3 |
| 2001/0053986 | A1 * | 12/2001 | Dick | 705/3 |
| 2002/0004727 | A1 * | 1/2002 | Knaus et al. | 705/3 |
| 2002/0016923 | A1 * | 2/2002 | Knaus et al. | 713/200 |
| 2002/0022975 | A1 * | 2/2002 | Blasingame et al. | 705/3 |
| 2002/0026328 | A1 * | 2/2002 | Westerkamp et al. | 705/2 |
| 2002/0029157 | A1 * | 3/2002 | Marchosky | 705/3 |
| 2002/0032583 | A1 * | 3/2002 | Joao | 705/2 |
| 2002/0116227 | A1 * | 8/2002 | Dick | 705/3 |
| 2002/0165736 | A1 * | 11/2002 | Tolle et al. | 705/3 |
| 2003/0046114 | A1 * | 3/2003 | Davies et al. | 705/3 |
| 2003/0050803 | A1 * | 3/2003 | Marchosky | 705/3 |
| 2004/0103000 | A1 * | 5/2004 | Owurowa et al. | 705/2 |
| 2004/0117215 | A1 * | 6/2004 | Marchosky | 705/3 |

OTHER PUBLICATIONS

Levitt, "What is the future of electronic patient communication?", Jul./Aug. 2001, IN Confidence, vol. 9, No. 4, p. 6–7.*

Berman, "Confidentiality for medical data miners", Nov. 2002, Artificial Intelligence in Medicine, p. 1–11.*

* cited by examiner

Primary Examiner—Emmanuel L. Moise
Assistant Examiner—Christopher Revak
(74) Attorney, Agent, or Firm—Kirton & McConkie; Michael F. Krieger

(57) ABSTRACT

Systems and methods for managing data in compliance with regulated privacy, security, and electronic transaction standards. Implementation of the present invention takes place in association with one or more computer devices that are used in a system to manage data in compliance with regulated privacy, security, and electronic transaction standards. In one implementation, the system includes a single point of entry for external and/or internal requests, and/or a single point of exit for transmissions of information, wherein the transmissions include individually identifiable patient information to legitimate patient-approved requests. Implementation of the present invention further embraces the de-identification of information that may be selectively used and/or sold. The de-identification prevents the identification of patients corresponding to the medical information, thus allowing the information to be useful while still preserving professional confidences. Moreover, implementation of the present invention embraces fully digital authorizations and consents for retrieval from external data sources.

19 Claims, 7 Drawing Sheets

MANAGING DATA IN COMPLIANCE WITH REGULATED PRIVACY, SECURITY, AND ELECTRONIC TRANSACTION STANDARDS

RELATED APPLICATIONS

This application claims priority to U.S. Provisional Patent Application Ser. No. 60/380,679 filed May 15, 2002, entitled MANAGING DATA IN COMPLIANCE WITH REGULATED PRIVACY, SECURITY, AND ELECTRONIC TRANSACTION STANDARDS.

BACKGROUND OF THE INVENTION

1. Field of the Invention

The present invention relates to information management. In particular, the present invention relates to systems and methods for managing data in compliance with regulated privacy, security, and electronic transaction standards.

2. Background and Related Art

Information management has become an important part of business practice. For example, in the medical arena, information is gathered from patients, physician services, medical research, medical training, insurance policy underwriting, and the like. The medical information has proven to be beneficial to patients, physicians, other medial service providers, and other business entities. For example, insurance companies that provide life, health, disability income, long term care, casualty, and reinsurance policies routinely require medical information for analysis as to policy eligibility. Typically, the analysis of medical information includes reviewing such medical records as an attending physician's statement, which is considered to be a very reliable record as it contains analyses and conclusions by a licensed medical professional. Medical records are also used in determining the amount of risk presented by an individual for a policy, and in determining causation and other issues relevant to insurance claim adjusting.

Currently, medical records are generally available, but are not easily accessible because of the confidential nature of the information. Accordingly, the medical records are protected by established professional conduct and by enacted legislation requiring the patient's consent prior to disclosure of the medical record information. Further, a large majority of the medical record information is restricted to paper documentation that is located in the office file rooms of the medical service providers, restricting the sharing of information.

In order to prevent the expense of filling office space with voluminous records, some medical providers are migrating to electronic record systems, and are converting paper records to electronic records. However, like their paper counterparts, the electronic records typically remain isolated from external sources.

Currently, a delay is generally experienced when requesting information from a medical information repository, such as a physician's office. The delay is due to the paper-only format of the records, the need for personnel time to pull the records and provide the requester with a copy thereof, and the low priority that is assigned to such requests by medical providers. Typically, the delay in underwriting insurance policies may cause applicants to lose interest, and cause a consequent loss of business to the insurer.

In an effort to shorten delays, some requesters utilize agents to travel to the various medical offices to manually retrieve copies of the medical records. Although this may partially accelerate the obtaining of the records, the cost in performing this service can be expensive and the technique does not address the problem of determining whether the retrieved record is complete, and whether other records exist. Moreover, even when the existence and location of a record are known, its relevance remains uncertain until retrieved and reviewed.

Health care providers and emergency medical technicians also have a need to access medical records. Health care providers and emergency medical technicians are typically required to make decisions regarding the care of a patient under circumstances in which paper records are unavailable. The inability for traditional techniques to provide medical record information to health care providers and emergency medical technicians increase the risk of improper treatment and the likelihood of medical malpractice.

A further complication in the providing of medical information to a particular requestor lies in the Health Insurance Portability and Accountability Act (HIPAA), which mandates regulations that govern privacy, security, and electronic transactions standards for health care information. The regulations require major changes in how health care organizations handle all facets of medical information management, including reimbursements, coding, security, and patient records. The regulations have a far-reaching impact on every department of every entity that provides or pays for health care.

For example, HIPAA requires that the medical entity enable patients to first view any and all patient-specific information that the entity may have concerning them, and that the medical entity enable patients to make annotations or comments pertinent to the information that the entity has provided. Further, patients may request that information be corrected. Accordingly, the entity is required to enable a patient-driven "editorial commenting" capability. While the medical entity is not necessarily obligated to make any actual "corrections" to their internal records, they are required to indicate that the patient has registered their comments or made certain suggested changes to their personal information.

Such requirements may generally be considered as a real detriment by many medical entities. Yet to others it represents an opportunity for the entity (e.g. a physician or others who may hold crucial clinical information, such as a prescription history) to document and publish the fact that the patient himself has actually viewed and verified as of a certain date the accuracy and completeness of their personal information that the entity has about them. In the case of retrieving and viewing a current prescription history, the patient-verified history would be very assuring to an emergency room physician that is treating the patient.

Accordingly, it would be an improvement in the art to enable affected entities to comply with the regulations that have been enacted, and to facilitate information management and exchange without breaching duties of confidentiality nor professional relationships.

SUMMARY OF THE INVENTION

The present invention relates to information management. In particular, the present invention relates to systems and methods for managing data in compliance with regulated privacy, security, and electronic transaction standards.

Implementation of the present invention takes place in association with one or more computer devices that are used in a system to manage data in compliance with regulated privacy, security, and electronic transaction standards. In one implementation, the system includes a single point of entry for external and/or internal requests, and/or a single point of exit for transmissions of information, wherein the transmissions include individually identifiable patient information to legitimate patient-approved requests. Implementation of the present invention further embraces the de-identification of information that may be selectively used and/or sold. The de-identification prevents the identification of patients corresponding to the medical information, thus allowing the information to be useful while still preserving professional confidences. Moreover, implementation of the present invention embraces fully digital authorizations and consents for retrieval from external data sources.

While the methods and processes of the present invention have proven to be particularly useful in the area of managing medical information, those skilled in the art can appreciate that the methods and processes can be used in a variety of different applications and in a variety of different areas of manufacture to manage information, such as academic information, financial information, and the like.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

The present invention relates to information management. In particular, the present invention relates to systems and methods for managing data in compliance with regulated privacy, security, and electronic transaction standards.

Embodiments of the present invention take place in association with one or more computer devices that are used in a system to manage data in compliance with regulated privacy, security, and electronic transaction standards. In one embodiment, the system includes a single point of entry for external and/or internal requests, and/or a single point of exit for transmissions of information, wherein the transmissions include individually identifiable patient information to legitimate patient-approved requests. Furthermore, embodiments of the present invention embrace fully digital authorizations and consents for retrieval from external data sources.

Embodiments of the present invention also embrace the de-identification of information that may be selectively used and/or sold. The de-identification prevents the identification of patients corresponding to the medical information, thus allowing the information to be useful while still preserving professional confidences.

The following disclosure of the present invention is grouped into two subheadings, namely "Exemplary Operating Environment" and "Managing Data in Compliance with Regulation Standards." The utilization of the subheadings is for convenience of the reader only and is not to be construed as limiting in any sense.

Exemplary Operating Environment

Figure 1:
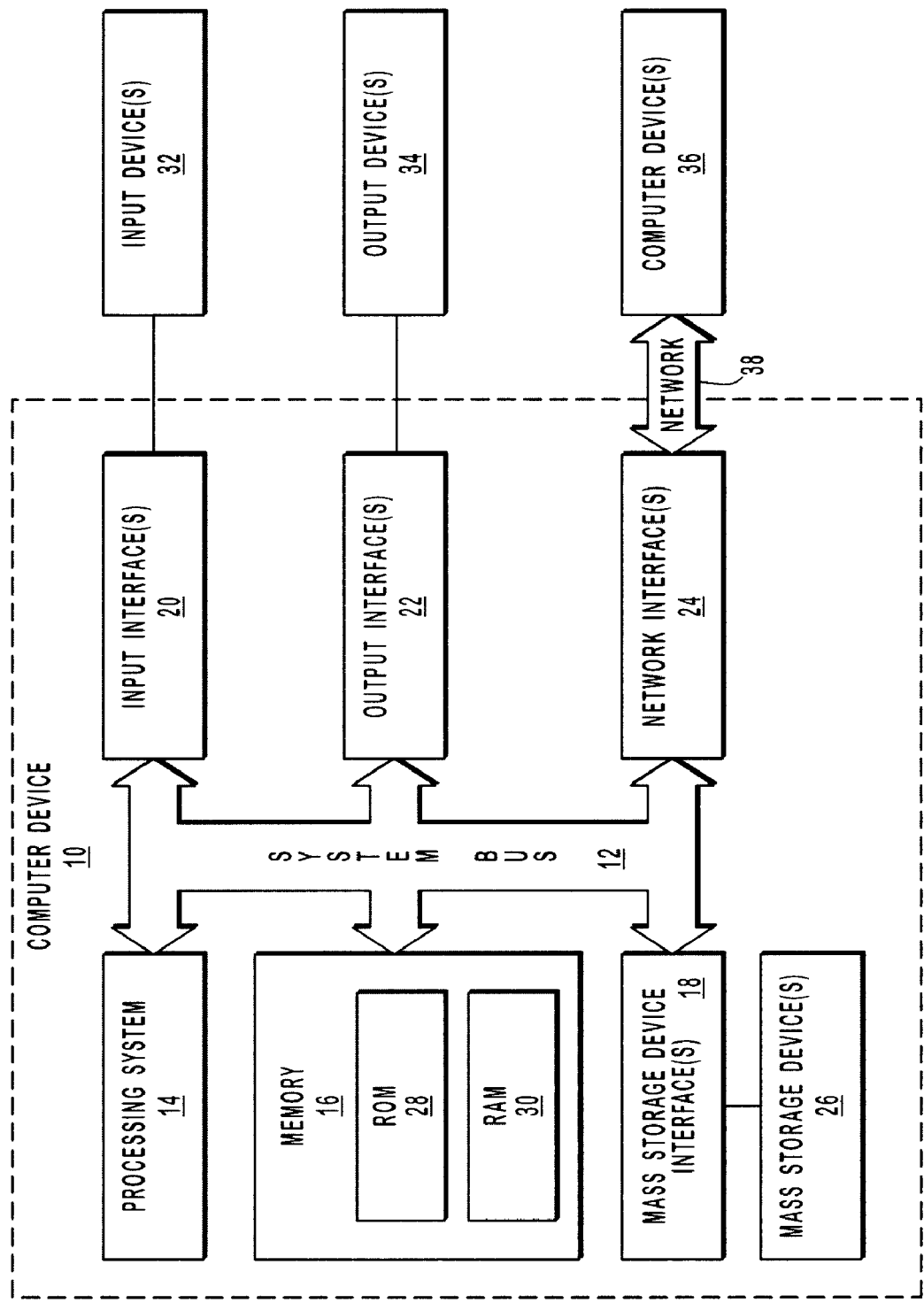
FIG. 1 illustrates a representative system that provides a suitable operating environment for use of the present invention.

FIG. 1 and the corresponding discussion are intended to provide a general description of a suitable operating environment in which embodiments of the invention may be implemented. One skilled in the art will appreciate that the invention may be practiced by one or more computing devices and in a variety of system configurations, including in a networked configuration.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative system for implementing the invention includes computer device 10, which may be a general-purpose or special-purpose computer. For example, computer device 10 may be a personal computer, a notebook computer, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), a firewire (IEEE 1394), or another interface.

One or more output interfaces 22 may be employed to connect one or more corresponding output devices 34 to system bus 12. Examples of output devices include a monitor or display screen, a speaker, a printer, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Figure 2:
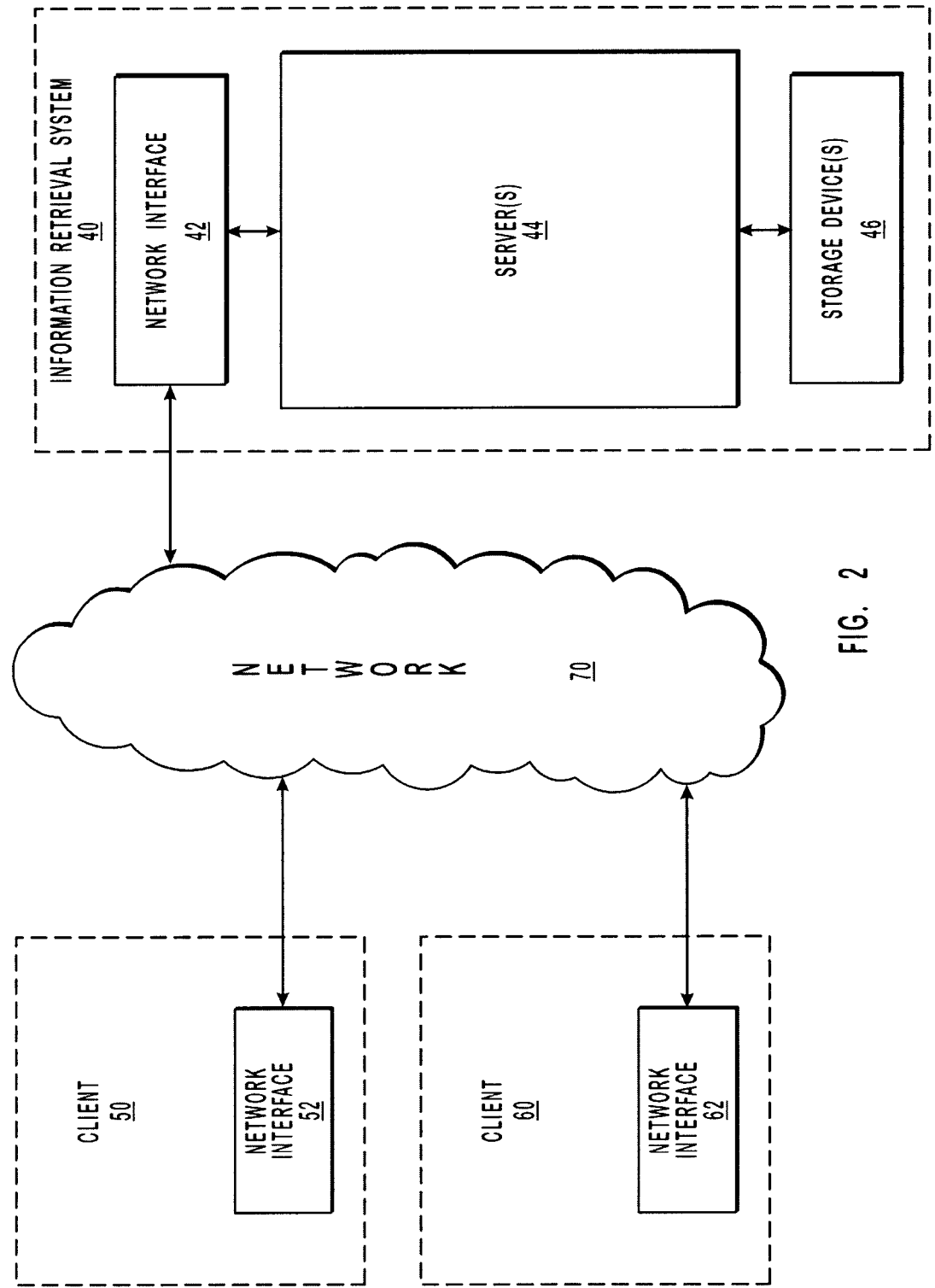
FIG. 2 illustrates a representative networked system that enables data management in compliance with regulated privacy, security, and electronic transaction standards in accordance with the present invention.

While those skilled in the art will appreciate that the invention may be practiced in networked computing environments with many types of computer system configurations, FIG. 2 represents an embodiment of the present invention in a networked environment that includes clients connected to a server via a network. While FIG. 2 illustrates an embodiment that includes two clients connected to the network, alternative embodiments include one client connected to a network or many clients connected to a network. Moreover, embodiments in accordance with the present invention include a multitude of clients throughout the world connected to a network, where the network is a wide area network, such as the Internet.

In FIG. 2, clients 50 and 60 exchange information with information retrieval system 40 via network 70. Such information exchanges include the submission of a request for information by a client to the information retrieval system. Such requests may be in the form of electronic data. Network interfaces 42, 52, and 62 enable the exchange of information between clients 50 and 60 and information retrieval system 40, which includes servers 44 and storage devices 46. In the illustrated embodiment, servers 44 process the methods disclosed herein to respond to requests by clients 50 and 60 as to the obtaining of information, which is preserved at storage device(s) 46. Once the requested information is selectively obtained, a report is preserved by system 40 and a copy of the report is transmitted back to the requestor in response to the request, as will be further discussed below.

Managing Data in Compliance with Regulation Standards

As discussed above, embodiments of the present invention take place in association with one or more computer devices that are used in a system to manage data in compliance with regulated privacy, security, and electronic transaction standards. In particular, embodiments of the present invention embrace a single point of entry for external and/or internal requests, and/or a single point of exit for transmissions of information.

Figure 3:
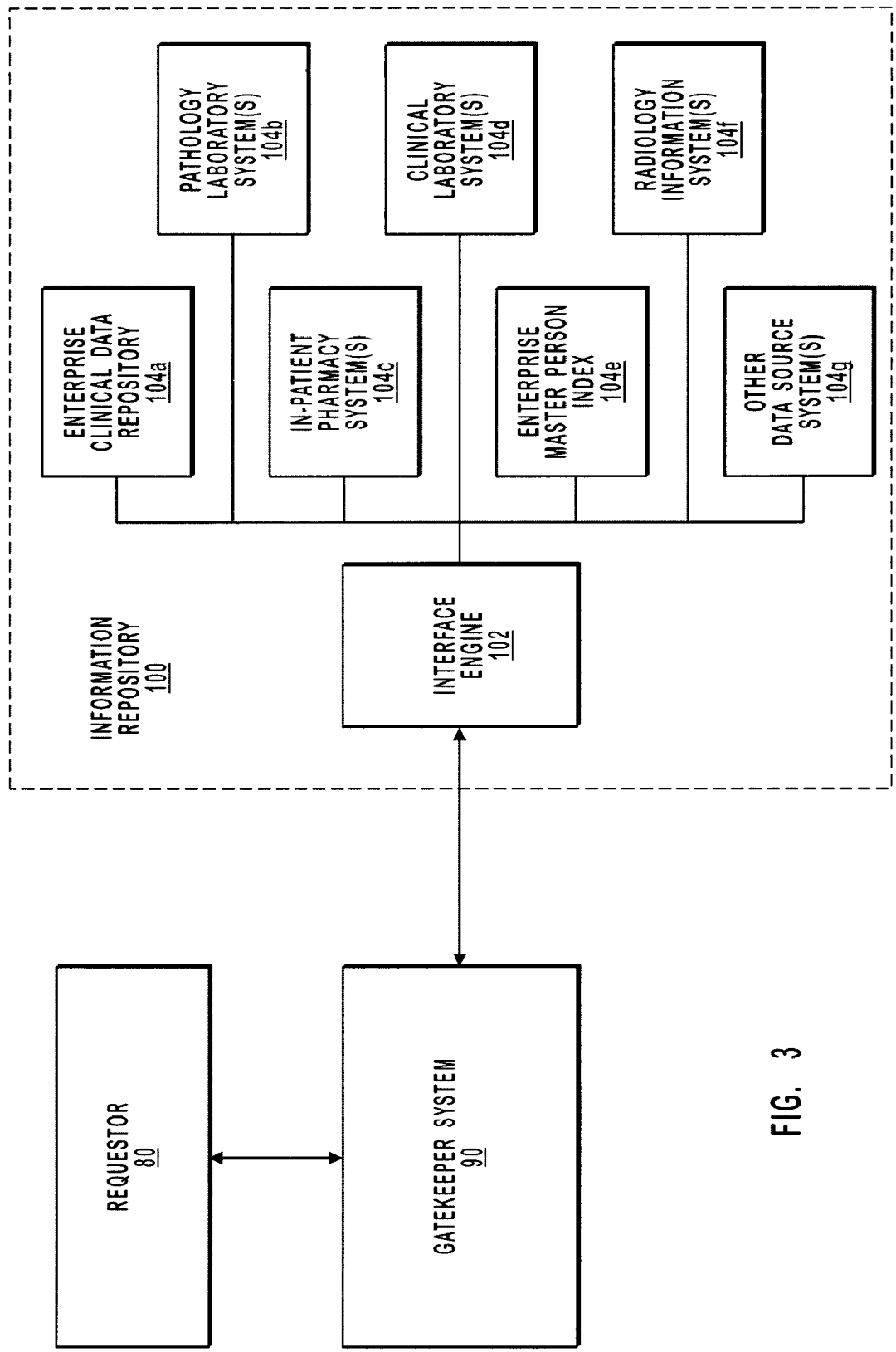
FIG. 3 illustrates a representative system that allows a requester to interface with a gatekeeper system to selectively obtain information from one or more of a variety of sources in an information repository.

With reference now to FIG. 3, a representative system is illustrated that allows a requestor 80 to interface with a gatekeeper system 90 to selectively obtain information from one or more of a variety of sources in an information repository 100. Requestor 80 represents any person or entity that desires to obtain information. Examples of such requesters include insurance companies, care providers, researchers, patients, and the like.

Enabling the Patient to View their Personal Information

For example, the requester 80 may request to see particular information from a covered medical entity. The enterprise provides for this capability via retrieval request and processing procedures that are afforded to the requestor (e.g. an insurance underwriter) who presents an authenticated authorization or signed consent by the patient. Therefore, the patients themselves may request a copy of any and all of their patient-specific information at any time. The entity responds by sending the information to the requestor in a timely manner.

In the illustrated embodiment, the information repository 100 includes a variety of information/data sources that may be located locally or remotely from eachother. The illustrated data sources include enterprise clinical data repository 104a, pathology laboratory system(s) 104b, in-patient pharmacy system(s) 104c, clinical laboratory system(s) 104d, enterprise master person index 104e, radiology information system(s) 104f, and other data source system(s) 104g. Accordingly, when information is requested, the data is selectively obtained from one or more of the data sources using an interface engine 102, which interfaces with gatekeeper system 90 to provide a report in response to requester 80.

As illustrated, gatekeeper system 90 provides a single point of entry for requests. The requests may be from external or internal requesters. Accordingly, anyone that is authorized enters requests through a single point of entry. In one embodiment, the point of entry receives fully-digital authorizations and consents for retrieval from external sources, bringing diverse external data feeds through the entry point to facilitate patient safety.

As will be further discussed below, processing performed by the enterprise to respond to requests received include processing an authenticated request for a copy of a patient-specific record. Embodiments of the present invention embrace the use of flags to facilitate processing. For example, a flag is set for the output of all retrieval functions to be in a desired format so that the entity may easily print the information/documents or electronically transmit them to the requestor in a format that is useful to the requestor. A flag is set in an index of gatekeeper system 90 and also in the specific record in the audit trail archive at gatekeeper system 90 that the request is, for example, a patient-driven request. A flag is set in the index of gatekeeper system 90 and also in the specific record in the audit trail archive of gatekeeper system 90 that the information in this record has not yet been commented upon by the patient.

Other processing includes the preparation of a cover page that includes specific information and instructions for the patient delineating their rights under a particular law or regulation. An internal reference number is assigned for a particular record so that it may be used to expedite the search for any future referencing of the record. A dedicated FAX number is used for conveyance of information via facsimile, including the actual cover sheet that used to send back comments if a response is provided via facsimile. The output is provided in a patient-specified format and transmitted to the patient in a secure manner.

Accordingly, when requests are received by gatekeeper system 90, the information is selectively obtained from one or more data sources, including locally at system 90, to provide the requested information to the requestor in the form of a report, as will be discussed below.

Embodiments of the present invention also embrace the ability of requesters, such as patients, to comment on the particular information. For example, patients may send their comments to the gatekeeper system via any number of ways or formats such as, via facsimile, standard courier, mail, electronically, etc. If sent by facsimile, a particular fax number may be provided and dedicated for the purpose of receiving requestor information. For example, in one embodiment it is a fax modem that is set to only receive facsimiles. Accordingly, the comments are received in a specific location assuring that they will not be lost.

When a response (e.g. comment) is received from a patient, the mechanisms for attaching any and all comments as if they were attached files to the original request/response is invoked and appears in the audit trail that will be discussed below. When information is received via a facsimile store, the images of the comments in a patient response file are stamped the corresponding time and date for incorporation into the record. In one embodiment, all flags and mechanisms that enable tracking of all interactions and communications with the patient are enabled and initiated.

Embodiments of the present invention embrace the managing of comments received from requestors, such as patients. For example, patients may respond in any number of ways and there are appropriate mechanisms to address and deal with their individual responses. In one embodiment, the entity is enabled to appropriately support dealing with all aspects of interactions with the patient as required under the enacted regulations. Examples include setting a flag to indicate that the patient has responded with the status set to the verification of the completeness and/or accuracy of the information, the providing of minor comments, the providing of substantial comments, additions made to records, requests made for changes to the information.

As illustrate in FIG. 3, once the requested information is obtained and is to be provided to the requestor, a single point of exit for the transmission of individually identifiable patient data that is sent out in response to legitimate patient-approved requests is provided by gatekeeper system 90. The single point of exit creates a revenue opportunity via completely certified, de-identified data. Accordingly, de-identified information can be selectively sold to a variety of buyers, such as pharmaceutical companies, insurance companies, researchers, etc. In one embodiment, the information provided is encrypted. When the information is not de-identified, the individually identifiable patient data is sent out in response to legitimate, authenticated, patient-approved requests.

In accordance with the present invention, information released to a requestor goes through the gatekeeper system. In other words, the information is not provided directly from the individual data sources to the requester. Instead, the information from the data sources goes through the gatekeeper system to provide the information as a report to the requestor.

Embodiments of the present invention embrace source data systems that are secure from electronic and physical intrusion. Organizations utilize a combination of biometric and digital signature technologies to control physical and electronic access.

As provided above, all requests for data from a requestor 80, whether received electronically or otherwise, are entered into the gatekeeper system for processing. This includes all requests regardless of their origin. For example, requests received via facsimile, including a signed authorization, are scanned into the gatekeeper system. Such documents are compressed, digitized images that are bound to the information that is retrieved, and both are included in an audit trail that is maintained by gatekeeper system 90.

Since system 90 is the exclusive mechanism for receiving incoming requests for information, it consolidates all facets of the requesting process, including validation, verification, and authentication of not only the requests but also the accompanying patient-signed authorization/consent. System 90 also provides the mechanisms to receive authenticated electronic requests from an entire industry (e.g., the insurance industry) and from all other legitimate, patient-authorized requestors, including the patients themselves. Accordingly, the system provides the tools to receive and respond to patient-initiated requests to retrieve, review, and comment on the data that the enterprise has on file for the patients. As a result, the system eliminates the burden on the data sources to provide the information directly to the requesters, and in accordance with established regulations.

Figure 4:
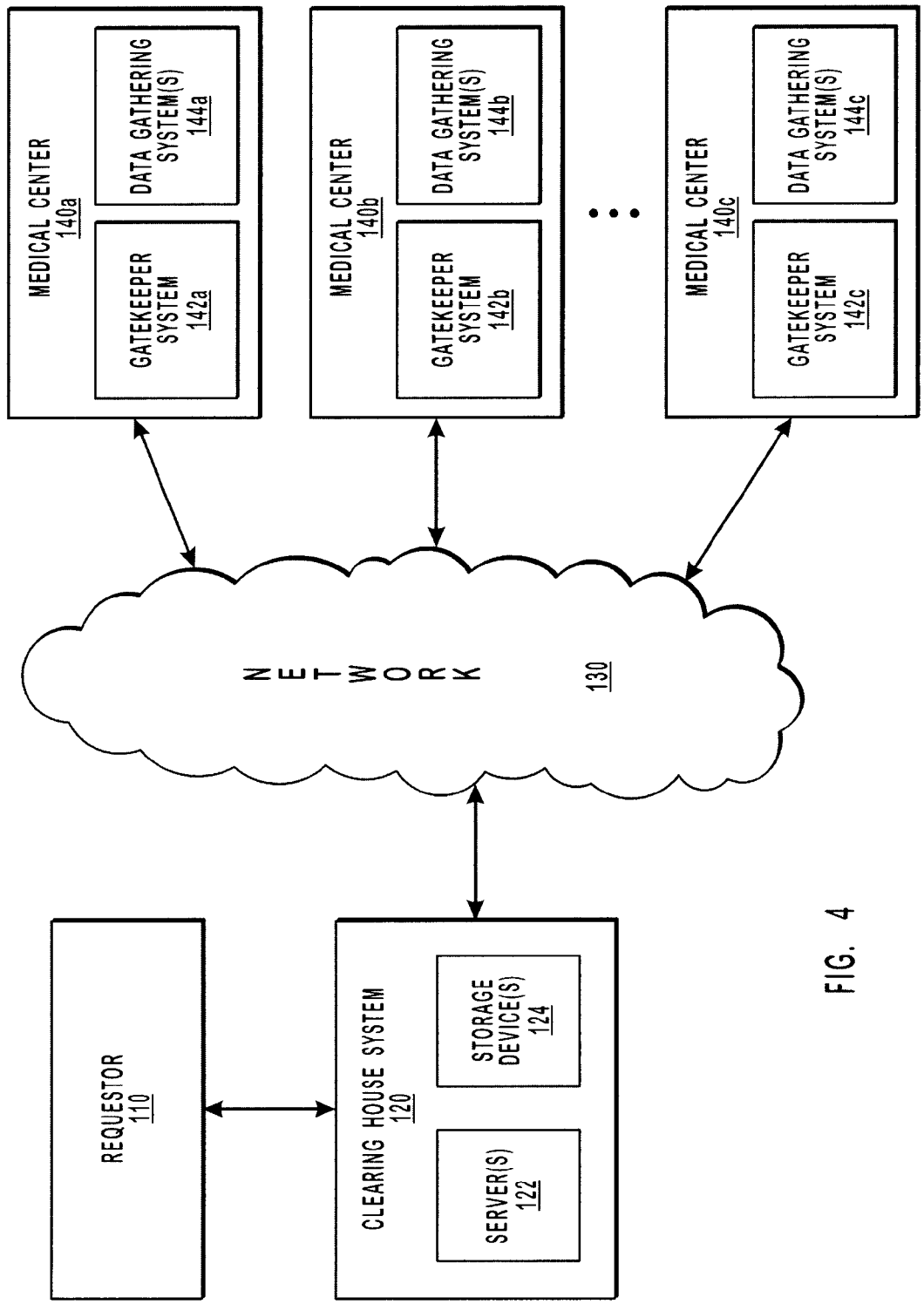
FIG. 4 illustrates a representative system that allows a requester to interface with a clearinghouse system, which is in communication with a variety of medical systems (e.g., hospitals, clinics, laboratories, etc.), wherein each medical system includes a corresponding gatekeeper system.

With reference now to FIG. 4, a representative system of the present invention is illustrated that allows a requestor 110 to interface with a clearinghouse system 120, which provides the single point of entry and the single point of exit. Clearinghouse system 120 includes one or more servers 122 and one or more storage devices 124, and is in communication with a variety of medical centers 140 (e.g., hospitals, clinics, laboratories, etc.), wherein each medical center 140 includes a corresponding gatekeeper system 142. In FIG. 4, each gatekeeper system 142 selectively provides information to clearinghouse system 120. A report is provided to requester 110 in response to a request. The information of the report is archived for a period of time (e.g., 6 years) to satisfy the time limit set by regulation.

Figure 5:
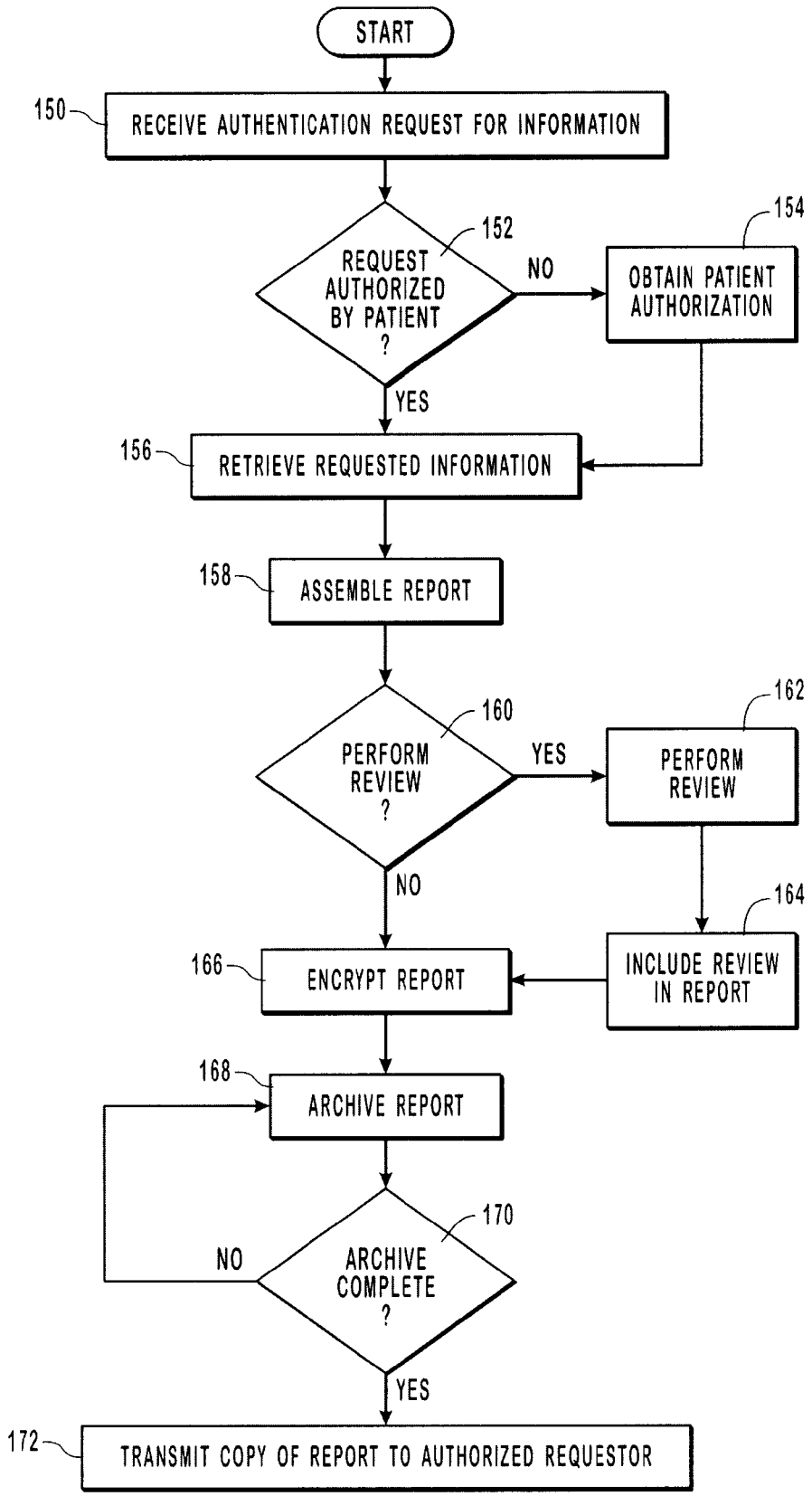
FIG. 5 illustrates a flowchart that provides a representative embodiment of processing that is performed to create, archive, and transmit a patient-specific report.

With reference now to FIG. 5, a flowchart is illustrated that provides a representative embodiment of processing that is performed to create, archive, and transmit a patient-specific report. In FIG. 5, execution begins at step 150, where an authenticated request for information is received. At decision block 152 a determination is made as to whether or not the request is authorized by the patient. If it is determined that the request is not authorized by the patient, execution proceeds to step 154, where patient authorization is obtained and then to step 156. Alternatively, if it is determined at decision block 152 that the request is authorized by the patient, execution proceeds directly to step 156.

In step 156 the requested information is retrieved. A report is then assembled at step 158. In one embodiment, the report includes such information as the request made, the response being provided, the corresponding audit trail, and other related information that is useful. A determination is made at decision block 160 as to whether or not to perform a review of the report. If it is determined at decision block 160 that a review of the report is to be performed, execution proceeds to step 162 for the performance of the review of the report, and then to step 164, where the review is included in the report. Execution then proceeds to step 166. Alternatively, it is determined at decision block 160 that a review is not to be performed on the report, execution proceeds directly to step 166.

At step 166 the report is encrypted and at step 168 the report is archived in a storage device. Execution then proceeds to decision block 170 for a determination as to whether or not the archive is complete. If it is determined that the archive is not complete, execution returns back to 168 to allow the report to be completely archived. Alternatively, if it is determined at decision block 170 that the archival of the report is complete, execution proceeds to step 172, where a copy of the report is transmitted to the authorized requester.

Figure 6:
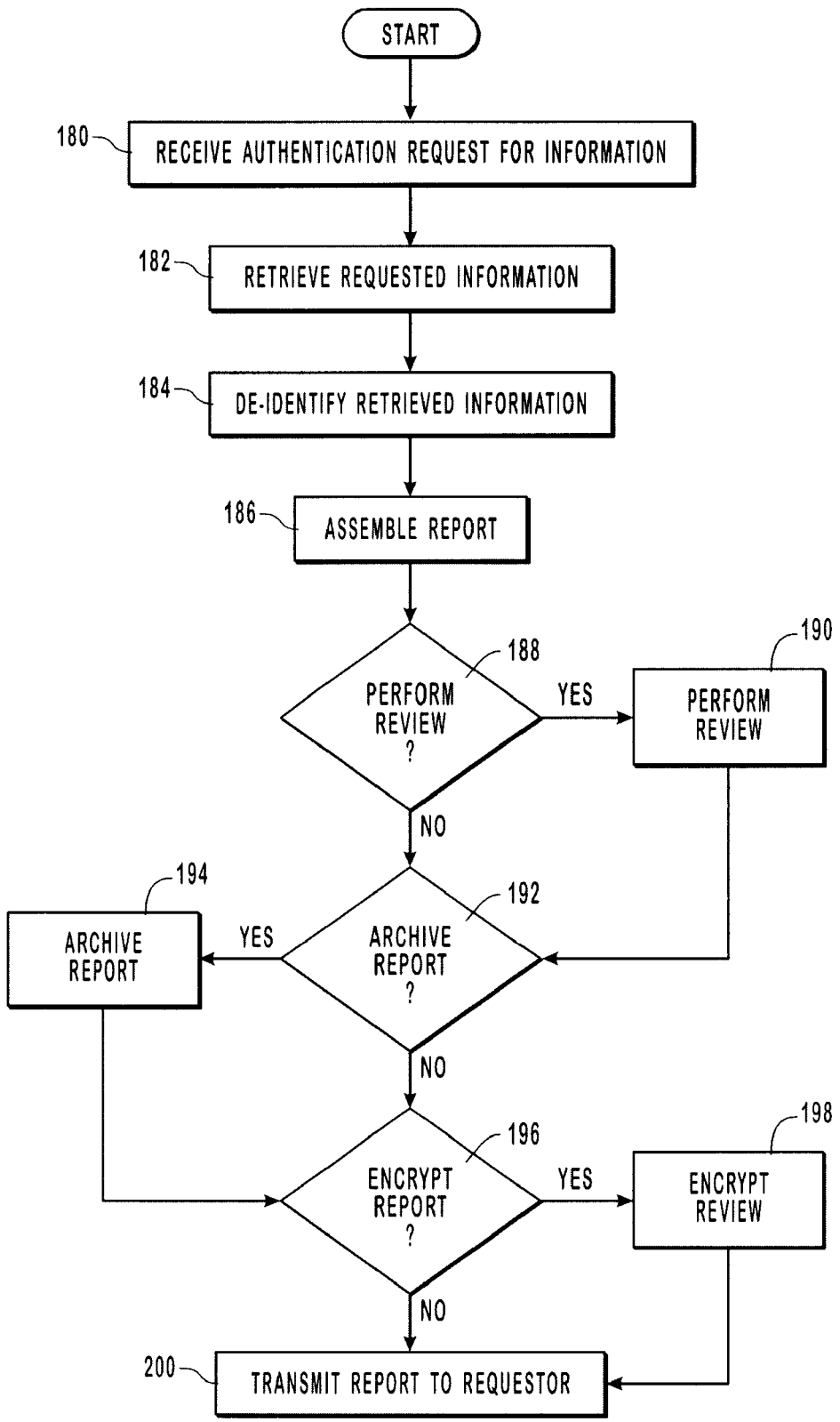
FIG. 6 illustrates a flowchart that provides a representative embodiment of processing that is performed to create, archive, and transmit a de-identified report.

FIG. 6 illustrates a flowchart that provides a representative embodiment of processing that is performed to create, archive, and transmit a de-identified report. In FIG. 6, execution begins at step 180, where an authenticated request for information is received. The requested information is then retrieved at step 182 and the retrieved information is de-identified at step 184. At step 186 the report is assembled. Execution then proceeds to decision block 188 for determination as to whether or not to perform a review. If it is determined at decision block 188 to perform a review, execution proceeds to step 190 for the performance of the review and then to decision block 192. Alternatively, it is determined at decision block 188 that a review is not to be performed execution proceeds directly to decision block 192.

At decision block 192 a determination is made as to whether or not to archive the report that has been assembled. If it is determined at decision block 192 that the report is to be archived, the execution proceeds to step 194 for the archival of the report and then to decision block 196. Alternatively, if it is determined at decision block 192 that the report is not to be archived, execution proceeds directly to decision block 196.

At decision block 196 a determination is made as to whether or not to encrypt the report that has been assembled. If it is determined at decision block 196 that the report is to be encrypted, execution proceeds to step 198 for the encryption of the report and then to step 200. Alternatively, if the report is not to be encrypted, execution proceeds directly to step 200, where the report is transmitted to the requester.

Figure 7:
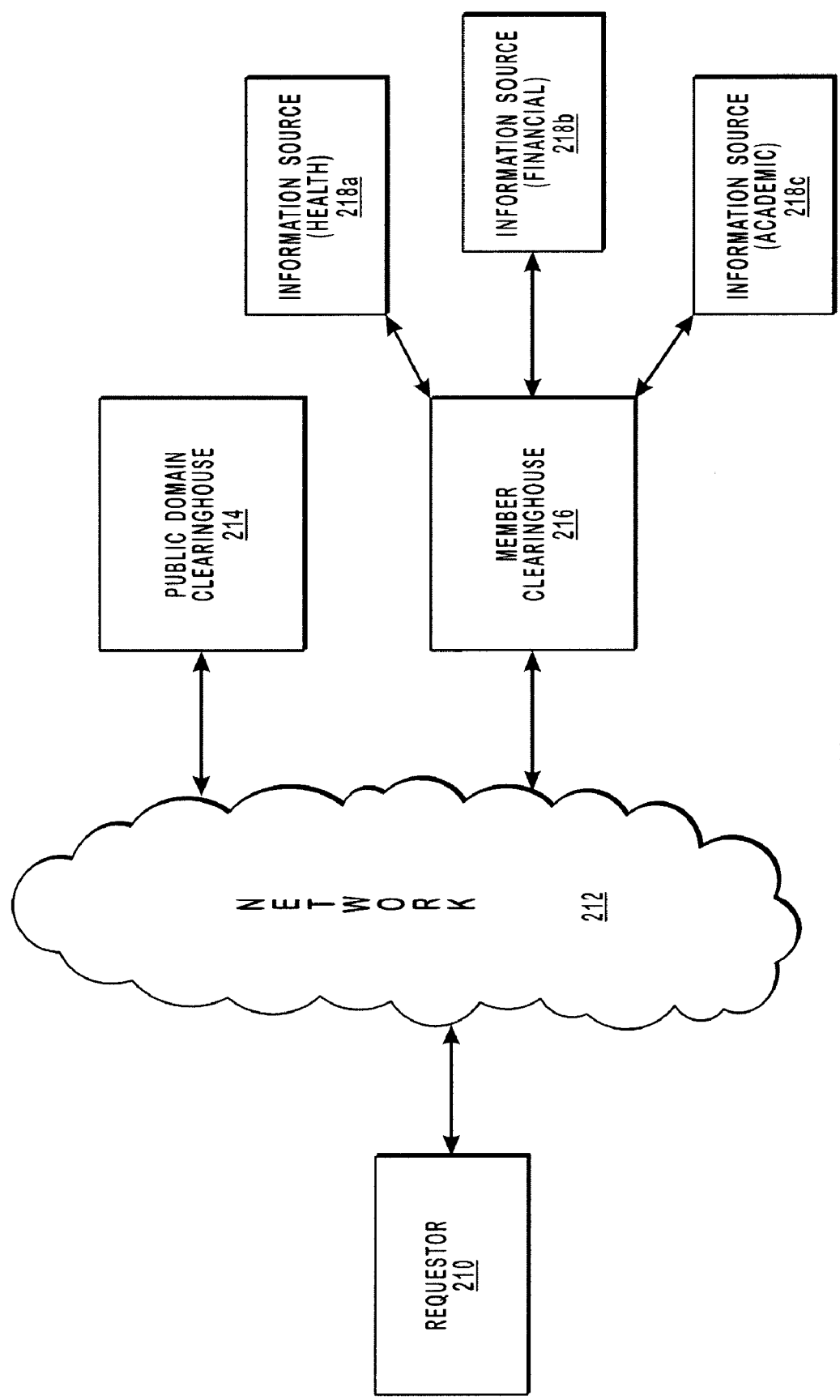
FIG. 7 illustrates a representative system that enables a requester to selectively obtain information from a public domain clearinghouse and/or a member clearinghouse, wherein the member clearinghouse enables members to update and/or modify personal information.

With reference now to FIG. 7, a representative system is illustrated that enables a requestor to selectively obtain information from a public domain clearinghouse 214 and/or from a member clearinghouse 216, wherein the member clearinghouse enables members to selectively update and/or modify personal information. Member clearinghouse 216 obtains information from information sources 218, which provide personal information, such as medical/health, financial, academic, and/or any other type of information that would be useful to a requester. The member clearinghouse provides a single point of entry and a single point of exit to manage and oversee the information that is provided to the requester.

Thus, as discussed herein, the embodiments of the present invention embrace information management. In particular, the present invention relates to systems and methods for managing data in compliance with regulated privacy, security, and electronic transaction standards. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. In a system that includes a computer device, a method for managing healthcare data in compliance with regulated privacy, security, and electronic transaction standards, the method comprising:
   receiving from a requestor a request for healthcare information relating to a patient, wherein any request is received through a single point of entry regardless of whether the request is from a requestor internal or external to a given healthcare facility;
   retrieving the requested healthcare information;
   assembling a report, wherein the report includes:
      the requested healthcare information;
      any comments of the patient received at a gatekeeper system regarding the requested healthcare information; and
      an audit trail; and
   transmitting a copy of the report to the requestor through a single point of exit regardless of whether the request was from a requestor internal or external to the given healthcare facility.

2. A method as recited in claim 1, wherein the request electronically authenticated to be authorized by the patient.

3. A method as recited in claim 1, further comprising the step for determining whether patient authorization exists for responding to the request, wherein if authorization from the patient has not been obtained, performing the step for obtaining authorization from the patient to provide the requested healthcare information.

4. A method as recited in claim 1, wherein the copy of the report includes patient specific healthcare information.

5. A method as recited in claim 1, further comprising the step for determining whether to provide de-identified healthcare information in response to the request, wherein if de-identified healthcare information is to be provided, performing the step for de-identifying the requested healthcare information.

6. A method as recited in claim 5, wherein the copy of the report includes de-identified healthcare information.

7. A method as recited in claim 1, further comprising the step for selectively performing a review of the report.

8. A method as recited in claim 1, further comprising the step for selectively encrypting the report.

9. A method as recited in claim 1, further comprising the step for selectively archiving the report.

10. A method as recited in claim 9, wherein the report is automatically archived for a period of time set by a regulation.

11. A system for managing healthcare data in compliance with regulated privacy, security, and electronic transaction standards, the system comprising:
   a computer system comprising:
      a gatekeeper system having:
         a single point of entry that is configured to selectively receive a request for healthcare information relating to a patient, wherein all requests are received through the single point of entry regardless of whether a requestor is internal or external to a given healthcare system facility; and
         a single point of exit that is configured to selectively provide a report in response to the request regardless of whether the requestor is internal or external to the given healthcare system facility, wherein the report includes the requested healthcare information relating to the patient, any comments of the patient received at the gatekeeper system regarding the requested healthcare information, and an audit trail; and
   at least one data source in communication with the computer system, wherein the at least one data sources comprises at least a portion of the requested healthcare information.

12. A system as recited in claim 11, wherein the computer system includes an interface engine.

13. A system as recited in claim 11, wherein the request is an electronic request.

14. A computer program product for implementing within a computer system a method for managing data in compliance with regulated privacy, security, and electronic transaction standards, the computer program product comprising:
   a computer readable medium for providing computer program code means utilized to implement the method, wherein the computer program code means is comprised of executable code for implementing the steps for:
      receiving from a requestor a request for healthcare information relating to a patient, wherein any request is received through a single point of entry regardless of whether the request is from a requestor internal or external to a given healthcare facility;
      retrieving the requested healthcare information;
      assembling a report, wherein the report includes:
         the requested healthcare information;
         any comments of the patient received at a gatekeeper system regarding the requested healthcare information; and
         an audit trail; and
      transmitting a copy of the report to the requestor through a single point of exit regardless of whether the request was from a requestor internal or external to the given healthcare facility.

15. A computer program product as recited in claim 14, wherein the computer program code means further comprises executable code for implementing the steps for:
   determining whether authorization from the patient exists for responding to the request; and
   if the authorization from the patient does not exist, obtaining electronic authorization from the patient to provide the requested information.

16. A computer program product as recited in claim 14, wherein the computer program code means further comprises executable code for implementing the steps for:
   determining whether to provide de-identified healthcare information in response to the request; and
   if de-identified healthcare information is to be provided, de-identifying the requested healthcare information.

17. A computer program product as recited in claim 14, wherein the computer program code means further comprises executable code for implementing the step for selectively encrypting the report.

18. A computer program product as recited in claim 14, wherein the computer program code means further comprises executable code for implementing the step for selectively archiving the report.

19. A computer program product as recited in claim 14, wherein the computer program code means further comprises executable code for automatically implementing the step for archiving the report for a period of time set by a regulation.

* * * * *